United States Patent [19]

Wang et al.

[11] Patent Number: 5,655,539

[45] Date of Patent: Aug. 12, 1997

[54] METHOD FOR CONDUCTING AN ULTRASOUND PROCEDURE USING AN ULTRASOUND TRANSMISSIVE PAD

[75] Inventors: Jianjun Wang, Columbus; Annette G. Bouska, Dublin, both of Ohio; Lonnie R. Drayer, Plant City, Fla.

[73] Assignee: Abbott Laboratories, Abbott Park, Ill.

[21] Appl. No.: 606,877

[22] Filed: Feb. 26, 1996

[51] Int. Cl.$^6$ ............................................. A61B 8/00
[52] U.S. Cl. ................... 128/663.01; 604/892.1; 73/644
[58] Field of Search ............... 128/663.01, 662.03; 604/892.1; 73/644

[56] References Cited

U.S. PATENT DOCUMENTS

| | | | |
|---|---|---|---|
| 3,946,599 | 3/1976 | Patt | 73/644 |
| 5,370,635 | 12/1994 | Strausak et al. | 604/248 |
| 5,494,038 | 2/1996 | Wang et al. | 128/662.03 |

OTHER PUBLICATIONS

Lipkovker, L.M. "Ultrasonic Transdermol Drug Delivery System," WO 94/08655 published 28 Apr. 1994.

*Primary Examiner*—Francis Jaworski
*Attorney, Agent, or Firm*—Brian R. Woodworth

[57] ABSTRACT

A method for conducting an ultrasound procedure on an object having a target surface. The method includes the step of providing an ultrasound probe having an acoustical wave emitting end portion. A pad for transmitting acoustical waves between the ultrasound probe and a target surface of an object also is provided. The pad includes a first layer having a first porous portion which defines first layer pores therethrough. The first layer pores have a first layer pore dimension. The pad further includes a second layer having a first porous portion which defines second layer pores therethrough. The second layer pores have a second layer pore dimension. The second layer is attached to the first layer so as to define a space therebetween. The first porous portion of the first layer overlies the first porous portion of the layer. An ultrasound couplant is disposed in the space defined between the first layer and the second layer. The ultrasound couplant has a molecule size which is less than or substantially equal to the first layer pore dimension, and which is less than or substantially equal to the second layer pore dimension. The method further includes the steps of placing the first porous portion of the second layer in contact with a target surface and placing the acoustical wave emitting end portion of the ultrasound probe in contact with the first porous portion of the first layer. The ultrasound probe is then activated.

15 Claims, 13 Drawing Sheets

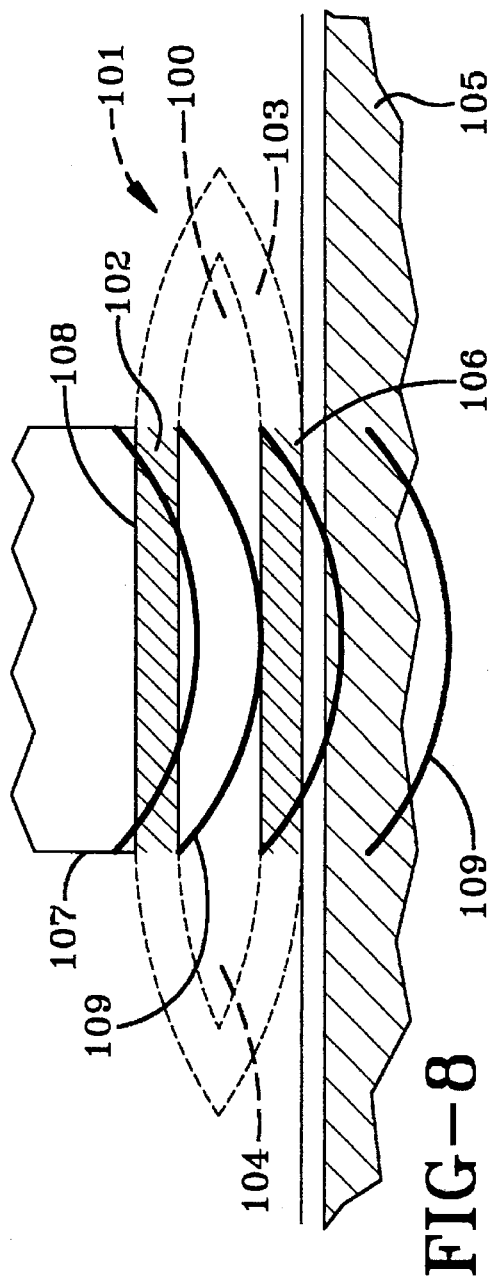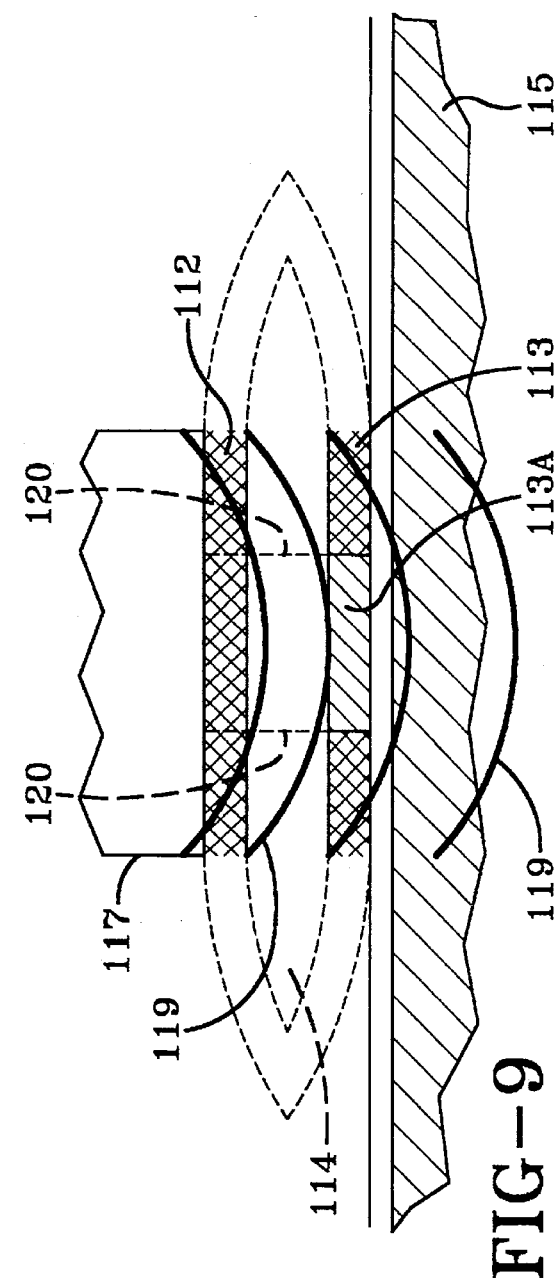

5,655,539

METHOD FOR CONDUCTING AN ULTRASOUND PROCEDURE USING AN ULTRASOUND TRANSMISSIVE PAD

BACKGROUND OF THE INVENTION

The present invention relates generally to a pad for use in the application of ultrasound energy to a target object. In particular, the present invention is directed to a pad that provides ultrasound transmissive contact between an ultrasound probe and a target object. The present invention further is directed to a method for the administration of medical compounds to target body tissues through the use of ultrasound energy and a pad containing a couplant containing one or more medical compounds.

Ultrasound imaging and pulse-echo technology have been widely used in the medical field for diagnostic testing and therapeutic purposes. Ultrasound imaging also has been used in industrial applications for the purpose of evaluating the structural integrity of castings and forgings in order to identify delaminations, voids, cracks, and deficiencies in weld integrity. Ultrasound imaging also has been used for the purpose of detecting spoilage or contamination of food products.

It has been discovered that ultrasound energy tends to cause a disorientation of a target tissue, thus increasing the permeability of the tissue and making possible the transdermal administration of a variety of substances. Transdermal drug deliver (TDD) offers several advantages over traditional drug delivery methods. For example, TDD avoids gastrointestinal drug metabolism, reduces elimination of the drug by the liver, and provides sustained release of the administrated drug. TDD also avoids the pain associated with drug injections and intravenous administration.

In order to utilize ultrasound imaging, it is necessary to establish an interface between the ultrasound probe and the target surface. This interface has commonly been created by placing a couplant gel between the probe and the target surface prior to directing ultrasound energy to the target surface. In the alternative, some systems create the requisite interface by directing a continuous stream of water between the target surface and the ultrasound probe. Finally, some systems employ an immersion technique in order to provide the requisite couplant.

Ultrasound gels are used as couplants in most medical applications of ultrasound energy. Use of these gels can be messy and labor-intensive. The continuous stream and immersion techniques are more typically used in industrial applications and require relatively sophisticated and expensive equipment in order to provide the requisite amount of water and to drain water that is used.

One method for eliminating the use of gels or flowing liquids as couplants entails the use of a dry couplant pad made of a compliant, encapsulated epoxy material attached as a facing to an ultrasound-transducer wedge. However, the solid couplant used in the pad tends to have a lower ultrasound energy transmission efficiency than a liquid or gel couplant.

SUMMARY OF THE INVENTION

The present invention is directed to a pad which acts as an ultrasound couplant between an ultrasound probe and a target surface. The pad includes first and second layers disposed in opposing relation to one another. At least a first portion of each of the first and second layers comprises a porous membrane material. The first porous portion of the first layer is disposed in opposing relation to the first porous portion of the second layer. The first and second layers are joined to one another so as to define a chamber therebetween. An ultrasound couplant is disposed within the chamber. The pores defined by the first porous portions of the first and second layers are at least substantially as large as the size of the molecules of the ultrasound couplant.

The present invention is further directed to a method for performing an ultrasound procedure using an ultrasound transmissive pad. The method includes the step of providing a pad having first and second layers disposed in opposing relation to one another. At least a first portion of each of the first and second layers comprises a porous membrane material. The first porous portion of the first layer is disposed in opposing relation to the first porous portion of the second layer. The first and second layers are joined to one another so as to define a chamber therebetween. An ultrasound couplant is disposed within the chamber. The dimension of the pores defined by the first porous portion of the first layer is larger than or substantially equal to the size of the molecules of the ultrasound couplant. The dimension of the pores defined by the first porous portion of the second layer is larger than or substantially equal to the size of the molecules of the ultrasound couplant. The method further includes the steps of placing the pad in contact with a target body tissue of a patient and providing an ultrasound probe. The ultrasound probe is placed in ultrasound transmissive contact with the first layer of the pad. In addition, the method of the present invention includes the step of activating the ultrasound probe. In medical applications of the method of the present invention, the tissue of the target body surface is disrupted by the ultrasound energy, thereby enabling the administration of a medical product through the tissue surface.

BRIEF DESCRIPTION OF THE DRAWINGS

For a more complete understanding of the present invention, reference may be had to the following Detailed Description read in connection with the accompanying drawings in which:

FIG. 8 is a cross-sectional view of a first embodiment of a pad constructed in accordance with the present invention;

FIG. 9 is a cross-sectional view of a second embodiment of a pad constructed in accordance with the present invention;

DETAILED DESCRIPTION

Figure 1:
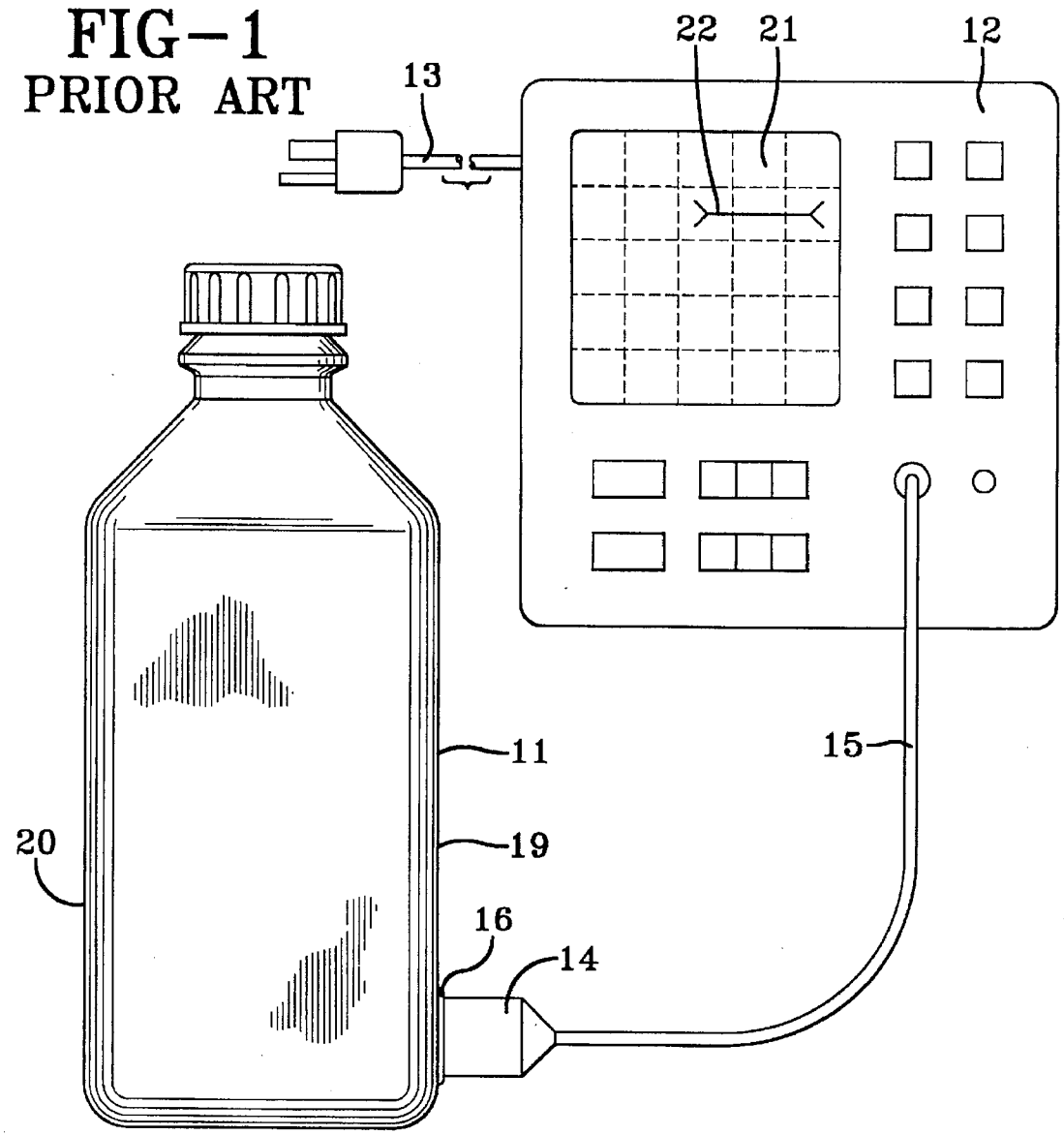
FIG. 1 is a representation of the use of ultrasound in testing for spoilage of a liquid nutritional product.
Figure 2:
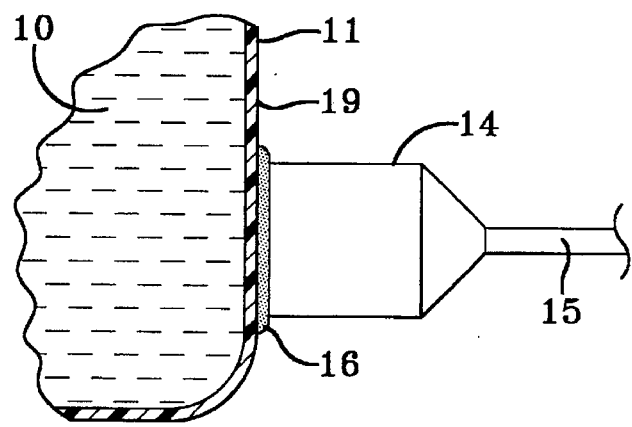
FIG. 2 is an enlarged, fragmentary view, partially in section, of the ultrasound testing process represented in FIG. 1.

FIGS. 1 and 2 depict a known application of ultrasound testing, i.e., for evaluating the physical characteristics of product 10 in container 11. Product 10 can be any of a variety of solid and/or liquid products, including liquid nutritional products. In the case of a liquid nutritional product, ultrasound testing can be used for the purpose of determining the presence of spoilage which is manifested by a change in the viscosity of the liquid or the formation of particles or globules in the liquid. Ultrasound operating system 12 is connected to an external power source by a power cord 13 or has an internal power supply such as an alkaline battery. As depicted in FIG. 1, ultrasound probe 14 is connected to ultrasound operating system 12 via transmission cable 15. In order to effect the ultrasound testing of product 10 in container 11, coupling gel 16 is applied to the exterior of first wall 19 of container 11. Ultrasound probe 14 is then brought in to physical contact with coupling gel 16 for the purposes of conducting the ultrasound test, wherein acoustical waves of a selected amplitude and frequency are produced by ultrasound probe 14 in a manner known in the art. The resulting acoustical waves are transmitted through coupling gel 16 and first wall 19 of container 11 and then pass into product 10. If no non-homogeneous conditions are present in product 10, the acoustical waves will impinge on opposing second wall 20 of container 11 and be reflected back to a receiver disposed within ultrasound probe 14. However, if the acoustical waves encounter globules, bubbles, particulate, or other non-homogenous conditions in product 10, the acoustical waves will be disrupted, thereby creating a different reflection pattern. Ultrasound operating system 12 transforms the reflected pattern into an electronic signal that can be imaged on screen 21 and/or transmitted to a controller and/or a recorder. The reflected pattern can be compared to a standard image 22 in order to determine the physical characteristics of product 10.

Figure 3:
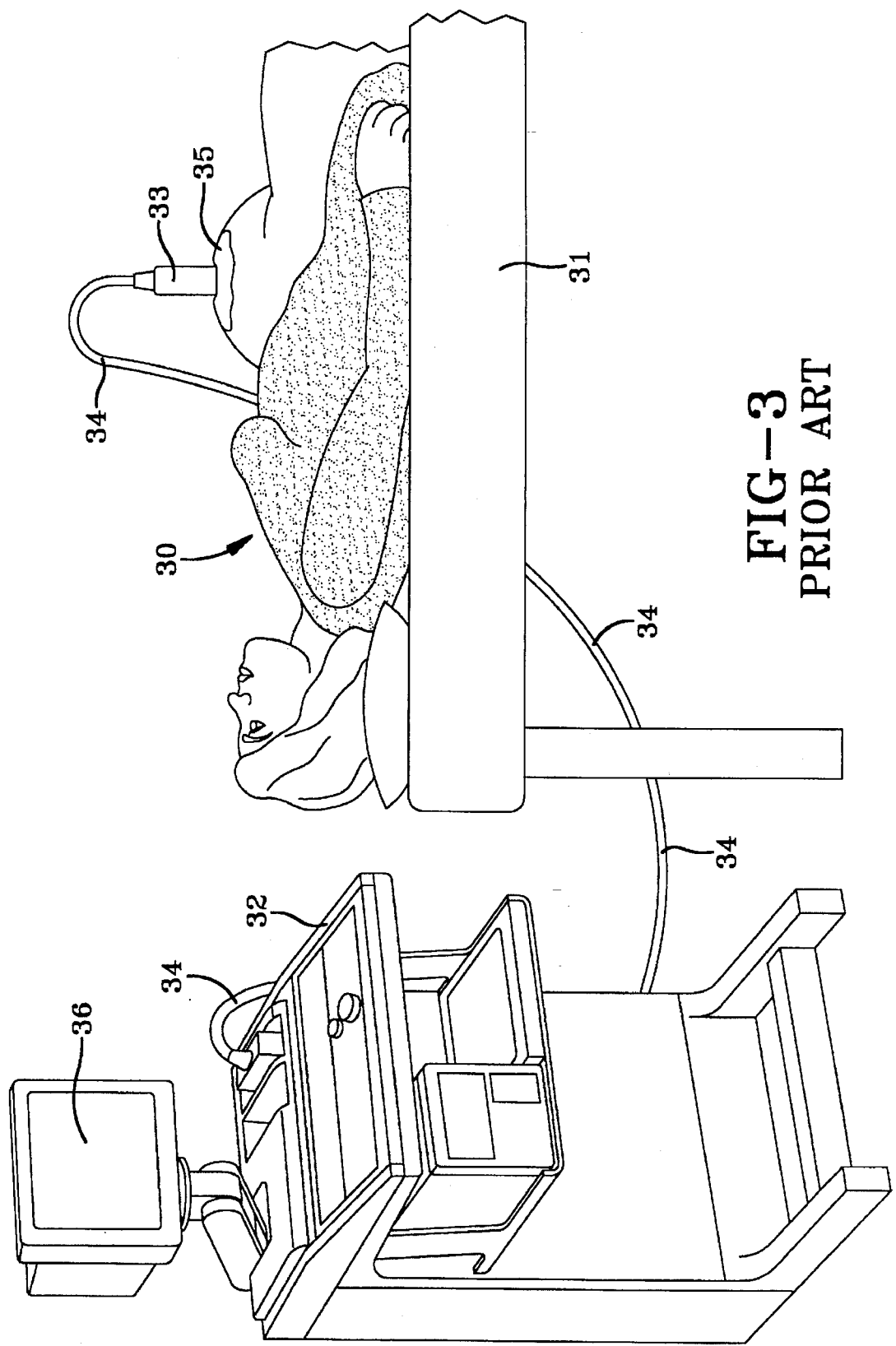
FIG. 3 is a plan view of a medical application of ultrasound technology.

FIG. 3 depicts a known medical application of ultrasound technology, i.e., the evaluation of a fetus in utero. Female patient 30 is shown in a reclining position and is supported on an examination surface such as table 31. Ultrasound operating system 32 is provided. System 32 is substantially identical to ultrasound operating system 12 depicted in FIG. 1. System 32 communicates with ultrasound probe 33 via a transmission cable 34. In this application, ultrasound probe 33 functions both as an ultrasound transducer and an ultrasound receiver. Suitable coupling gel 35 is applied to the skin of the abdomen of female patient 30. Ultrasound probe 33 is then placed in contact with coupling gel 35. Activation of ultrasound probe 33 causes acoustical waves of a selected amplitude and frequency to emanate from probe 33. The acoustical waves pass through coupling gel 35, the skin of patient 30, the abdominal tissue of patient 30, the uterus wall of patient 30, and the amniotic fluid within the uterus to impinge upon the fetus. The acoustic waves are then reflected back through the same media to the receiver of ultrasound probe 33. Ultrasound operating system 32 then transforms the reflected acoustical waves into an electronic signal which can be projected on a screen 36 as an image of the fetus. Such ultrasound technology can be used to produce images of other anatomical features of a patient.

Figure 4:
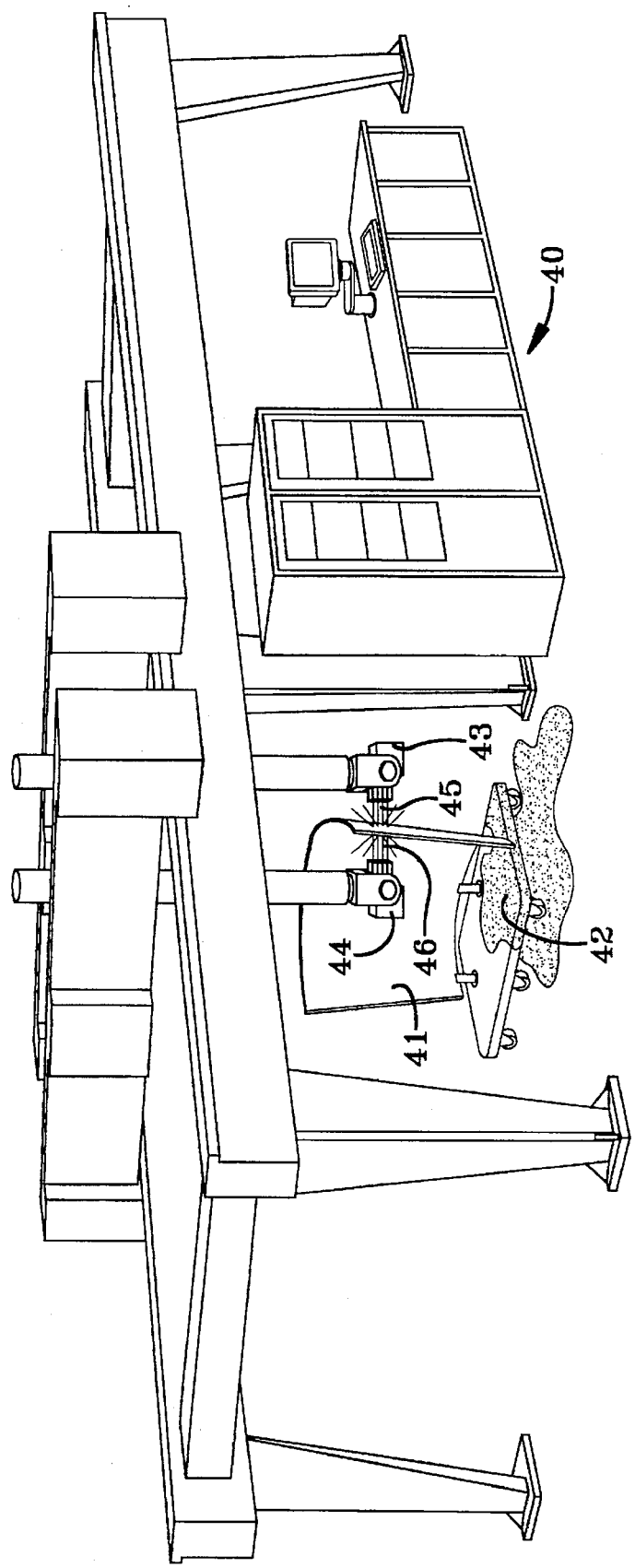
FIG. 4 is a plan view of a first industrial application of ultrasound technology.

FIG. 4 depicts ultrasound operating system 40 adapted for use in evaluating the structural integrity of object 41. Object 41 can be placed upon a suitable workpiece holding fixture 42 that may have wheels, as shown in FIG. 4. An ultrasound transducer is located in a first module 43 and a receiver is located in a second module 44. Modules 43, 44 are spaced apart such that object 41 can be placed therebetween. Streams of water 45, 46 are sprayed from modules 43, 44 to impinge upon object 41. Streams 45, 46 act as couplants for the transmission of the acoustical waves from first module 43 to object 41 and from object 41 to second module 44. Separate transmission cables extend between first and second modules 43, 44 and ultrasound operating system 40. Acoustical waves generated by the transducer in first module 43 are transmitted through stream 45, object 41, and second stream 46, and are received by a receiver located in second module 44. A system of the type depicted in FIG. 4 is described in U.S. Pat. No. 4,726,231 which is incorporated herein by reference.

Figure 5:
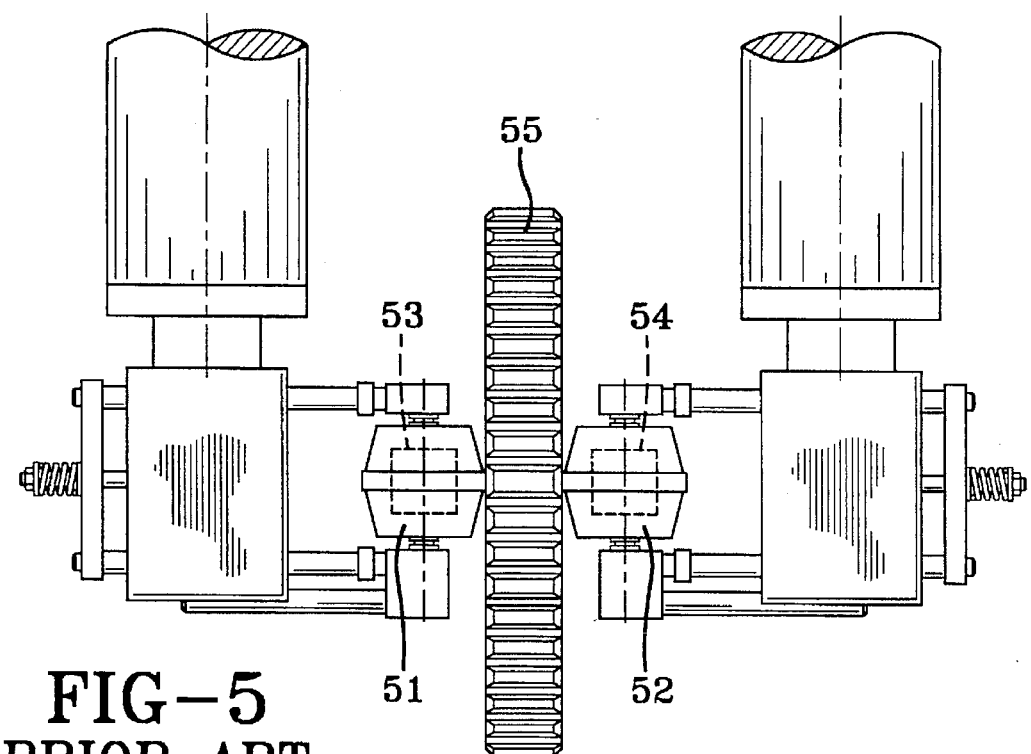
FIG. 5 is a plan view of a second industrial application of ultrasound technology.
Figure 6:
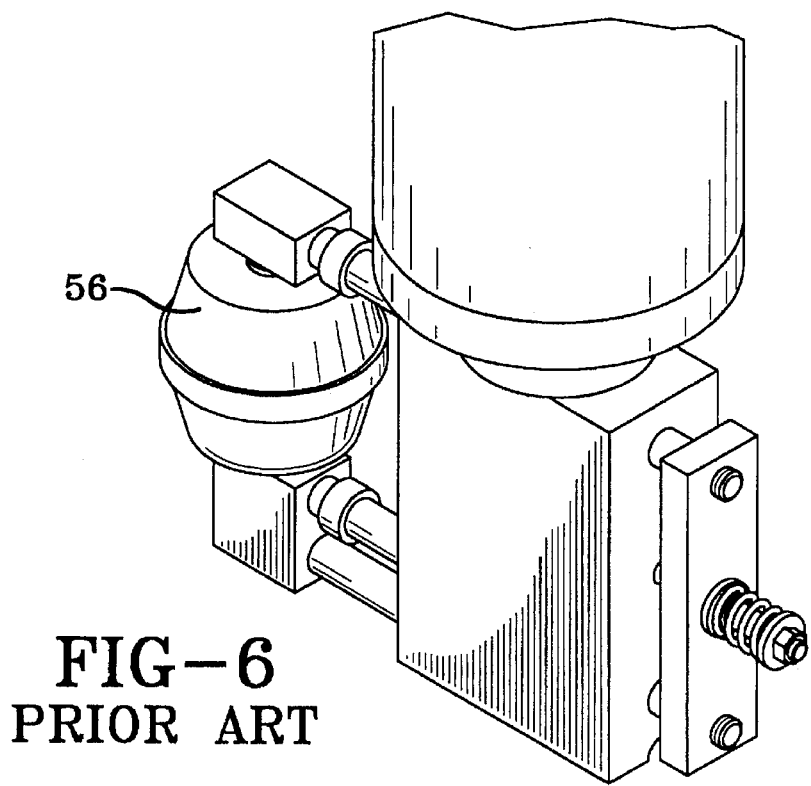
FIG. 6 is an enlarged view of a roller type of ultrasound probe module.

FIGS. 5 and 6 depict views of an ultrasound imaging system of the type depicted in FIG. 4 wherein the modules and associated streams of liquid have been replaced by first and second dry contact roller probes 51, 52. FIG. 5 also depicts a test piece 55 disposed between dry contact roller probes 51, 52. Probes 51, 52 are oriented such that they can traverse test piece 55 while remaining aligned with respect to one another. First dry contact roller probe 51 has ultrasound transducer 53 disposed therein and second dry contact roller probe 52 has receiver 54 disposed therein. In an alternative embodiment, a single contact roller 56 is provided, and the ultrasound transducer and receiver are disposed in the same contact roller 56. Roller probes 51, 52 are coated with a solid material having ultrasound acoustic wave transmission properties.

Figure 7:
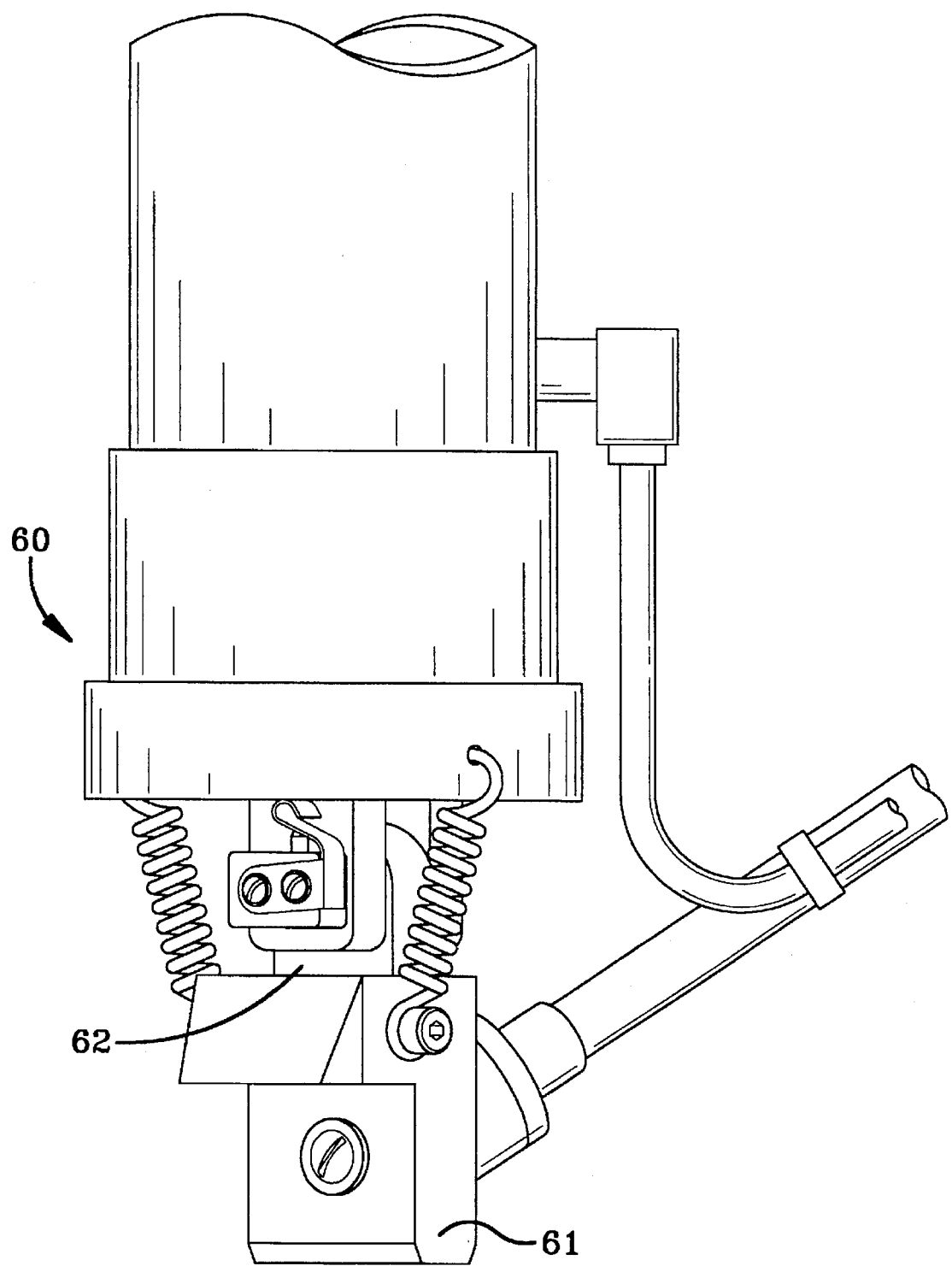
FIG. 7 is a plan view of a prior art ultrasound testing device.

FIG. 7 depicts a plan view of an ultrasound testing apparatus 60 wherein a dry contact acoustical couplant solid material 61 is used as an interface between an ultrasound transducer wedge (ultrasound probe) 62 containing both an ultrasound transducer and a receiver. As discussed in "Shear-Wave Ultrasound Inspection With a Dry Couplant," *NASA Tech Briefs*, December, 1994, pp. 77-78, the ultrasound transducer wedge 62 and couplant material 61 are pressed against a workpiece and the transducer is then activated in order to effect ultrasound imaging in the same manner above-described with respect to FIGS. 1-6.

As used herein, the term "ultrasound probe" refers to a device that is capable of transmitting and/or receiving ultrasound waves. There are two well-known and widely used types of ultrasound probes, i.e., "single type" and "array type" probes. A "single type" probe has a single ultrasound transducer and/or while an "array type" transducer has a plurality of ultrasound transducers and/or arranged either in a line or in a matrix array. Both single and array types of ultrasound probes can be used in the practice of the present invention. In addition, the apparatus and method disclosed herein can be used in any application of ultrasound technology, including, but not limited to, each of the above-discussed applications.

Figure 10:
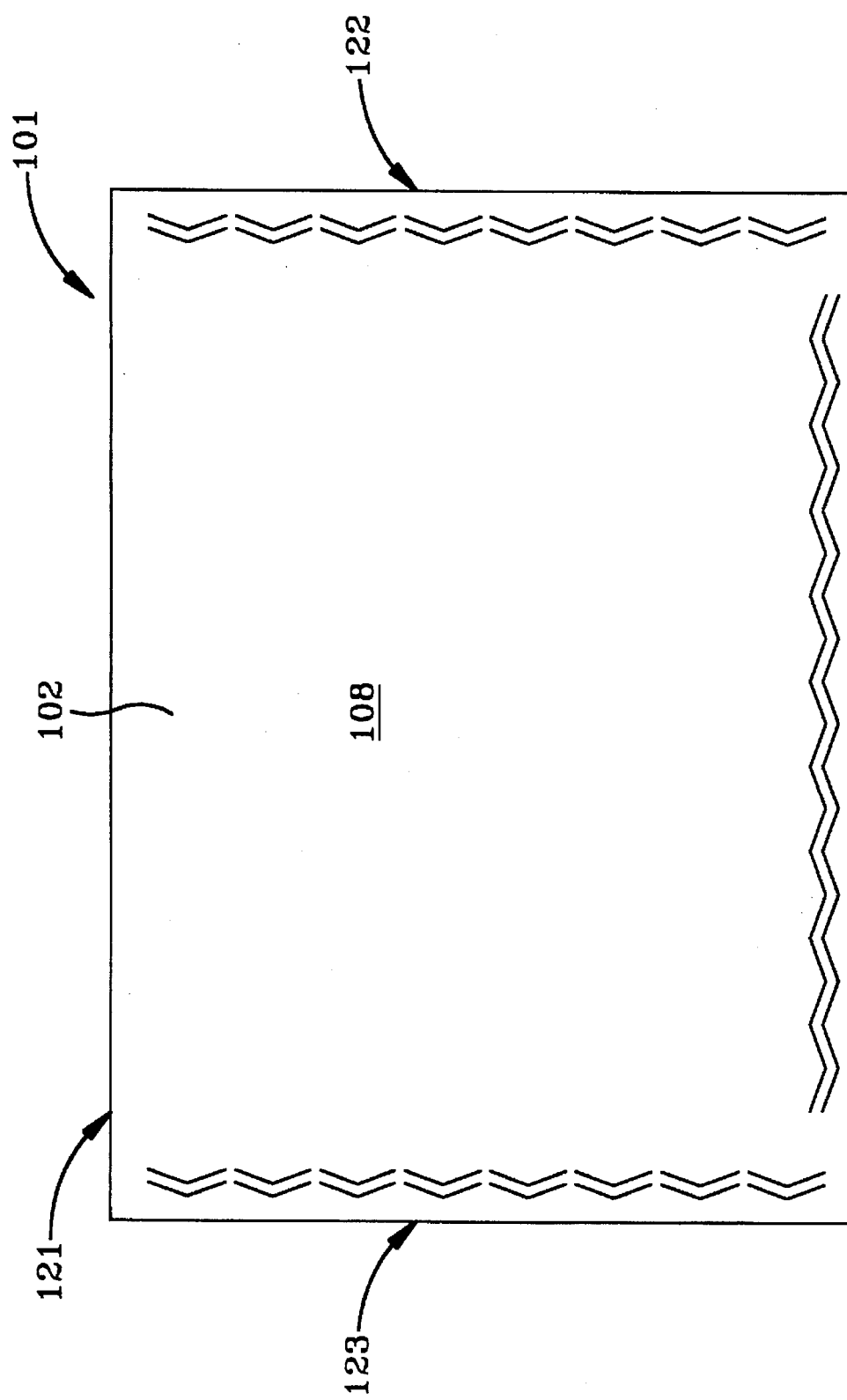
FIG. 10 is a top plan view of a pad constructed in accordance with the present invention.
Figure 13:
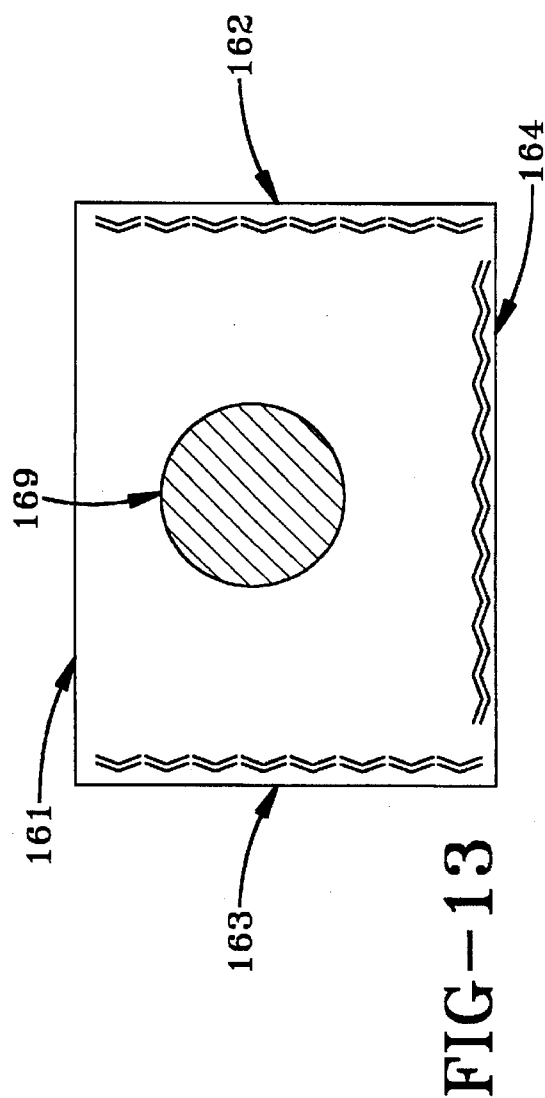
FIG. 13 is a top plan view of the pad of the third embodiment of the present invention.

Pad 101 constructed in accordance with the present invention is depicted in FIG. 8. Pad 101 includes first layer 102 and second layer 103. First and second layers 102, 103 are preferably bonded to one another to define space 104 therebetween. First and second layers 102, 103 can be formed from two separate pieces of material bonded to one another to define space 104. Alternatively, first and second layers 102, 103 can be formed from a single piece of material which is folded and bonded to itself about to define space 104. FIG. 10 depicts such a configuration of pad 101 wherein a single sheet of material is folded alone line 121 and bonded about edges 122, 123, and 124 in order to define space 104. FIG. 13 also depicts such a configuration of pad 101 wherein a single sheet of material is folded along line 161 and sides 162, 163, and 164 are bonded to one another to define space 104. In another alternative configuration, first and second layers 102, 103 can be provided by a single piece of extruded material that is flattened to the shape depicted in FIG. 8 and the remaining open ends bonded to one another to define space 104. It will be appreciated by one of ordinary skill in the art that a variety of known bonding techniques can be used, including, but not limited to, adhesive bonding and ultrasound welding, and that the particular bonding technique used will be determined by the type of material used in first and second layers 102, 103 and the personal preferences of the manufacturer and the user of pad 101.

Couplant 100 is disposed within space 104 defined between first and second layers 102, 103. Couplant 100 can be a variety of known ultrasound couplant materials including, but not limited to, water, glycerine, and silicone oil. Couplant 100 typically has a molecule size of 0.01–0.5 microns. Couplant 100 can further include other components that can be dissolved in or suspended in couplant 100, such as pharmaceutical and imaging agents, as discussed in greater detail herein.

As described in detail herein, first and second layers 102, 103 are constructed in whole or in part of porous membrane materials. For the purposes of this disclosure, the term "porous" refers to materials that are naturally porous as well as materials having apertures or other forms of flow pathways formed therethrough. The porous membrane materials used in connection with the present invention can be rigid, but preferably are flexible in order to fit the contour of the surface of the ultrasound probe and the target surface. The porous material is preferably pressure resistant such that it performs like a tight-meshed, multi-layered sieve. The porous material also preferably has acoustical wave transmitting characteristics which are similar to those of couplant 100. Mesh materials constructed of polytetrafluoroethylene or stainless steel can be used in connection with the present invention. Materials such as polytetrafluoroethylene are hydrophobic until treated with a wetting agent, e.g., isopropyl alcohol, and are particularly suited to medical applications of the present invention due to the fact that pad 101 will maintain couplant 100 in a sterile environment until isopropyl alcohol (or another wetting agent) is applied to pad 101. It will be appreciated that isopropyl alcohol is commonly used in medical applications to provide sterility. It is believed that silicone can be used in construction of first and second layers 102, 103 of the present invention. In order to identify the porous portions of first and second layers 102, 103, indicia 169 can be placed on an exterior surface thereof as depicted in FIG. 13.

In the embodiment of the present invention depicted in FIG. 8, first and second layers 102, 103 are constructed of a porous membrane material defining pores therethrough. The pores preferably have a size at least as great as the size of molecules of couplant 100, i.e., at least 0.01–0.5 microns, such that couplant 100 can becomes entrained in or passes therethrough. The particular pore size used in connection with the present invention is determined by the molecule size of couplant 100 used and by the desired rate of flow of couplant 100 through first and second layers 102, 103. For example, the pore size of first and second layers 102, 103 is preferably either substantially equal to the molecule size of couplant 100 (when it is desirable to entrain couplant 100 in first and second layers 102, 103) or slightly greater than the molecule size of couplant 100 (when it is desirable to provide for flow of couplant 100 through first and second layers 102, 103). For example, it is preferable that the size of the pores in first and second layers 102, 103 be in the range of 0.01–0.6 microns. This range of pore sizes is applicable to all embodiments of the present invention disclosed herein.

In a first configuration of the embodiment of the present invention depicted in FIG. 8, the pore size of first and second layers 102, 103 is substantially equal to the molecule size of couplant 100 such that couplant 100 becomes substantially entrained in first and second layers 102, 103. Because couplant 100 is entrained within first and second layers 102, 103 and is contained in space 104, pad 101 provides ultrasound transmissive contact between ultrasound probe 107 in contact with upper surface 108 of first layer 102 and a target surface 105 in contact with surface 106 of lower layer 103. However, because there is no flow of couplant 100 from pad 101, target surface 105 and ultrasound probe 107 will not be wetted by couplant 100. This aspect of the present invention is particularly advantageous in those applications where couplant 100 will damage or alter target surface 105, e.g., ceramics and timber. This aspect of the present invention also reduces the labor required in performing ultrasound procedures by eliminating the need to clean couplant 100 from target surface 105.

In a second configuration of the embodiment of the present invention depicted in FIG. 8, the pore size of first and second layers 102, 103 is greater than the molecule size of couplant 100, thereby facilitating flow of couplant 100 through first and second layers 102, 103.

In a third configuration first and second layers 102, 103 have differing pore sizes, e.g., first layer 102 has a pore size substantially equal to the molecule size of couplant 100 and second layer 103 has a pore size greater than the molecule size of couplant 100, whereby couplant 100 is substantially entrained in first layer 102 and whereby couplant 100 flows through second layer 103. In the alternative, first layer 102 can have a pore size greater than the molecules size of couplant 100 and second layer 103 can have a pore size substantially equal to the molecule size of couplant 100, whereby couplant 100 flows through first layer 102 and whereby couplant is substantially entrained in second layer 103.

In an alternative embodiment of the present invention depicted in FIG. 9, second layer 103 includes first portion 113 and second portion 113A. First portion 113 and second portion 113A are constructed of materials having differing porosities. In a first configuration of this alternative embodiment of the present invention, second portion 113A is constructed of a porous material having a pore size such that couplant 100 is entrained therein or passes therethrough while first portion 113 of second layer 103 is constructed of a material that is non-porous to couplant 100, thereby preventing couplant 100 from becoming entrained in or passing through second portion 113A. It will be appreciated that first portion 113 can be constructed of a porous material, provided that such material does not have pores of sufficient size to permit couplant 100 to become entrained therein or to pass therethrough. First layer 112 in this configuration is constructed of a material having a porosity such that couplant 100 in space 114 can become entrained in or pass therethrough. In this configuration of the embodiment of the present invention depicted in FIG. 9, an acoustical wave pathway 120 is defined through space 114 due to the fact that couplant 100 is not present in first portion 113 of second layer 103. That is, only the portion of acoustical waves 119 that passes through second portion 113A of second layer 103 will be passed from ultrasound probe 117 to target surface 115. Changes to the size and/or shape of second portion 113A of second layer 103 will alter the portion of acoustical wave 119 that reaches target surface 115 by altering acoustical wave pathway 120. It also will be appreciated that the amount of couplant 100 that becomes entrained in or passes through second layer 103 can be controlled by adjusting the size of second portion 113A, i.e., the larger the area of second portion 113A, the greater the flow rate through second layer 103.

In a second configuration of the embodiment of the present invention depicted in FIG. 9, first portion 113 of second layer 103 is constructed of a porous material having a pore size substantially equal to the molecule size of couplant 100 disposed in space 114 such that couplant 100 becomes entrained in first portion 113 of second layer 103. Second portion 113A of second layer 103 is constructed of a porous material having a pore size sufficient to permit the passage of molecules of couplant 100 therethrough. In this way, couplant 100 simultaneously becomes entrained in first portion 113 of second layer 103 and passes through second portion 113A of second layer 103. In this configuration, first layer 112 is constructed of a material having pores substantially equal in size to the molecule size of couplant 100 such that couplant 100 becomes entrained in first layer 112. In this configuration of the embodiment depicted in FIG. 9, pad 101 does not limit the size of acoustical pathway 120 because couplant 100 is entrained in first portion 113 of second layer 103.

Figure 11:
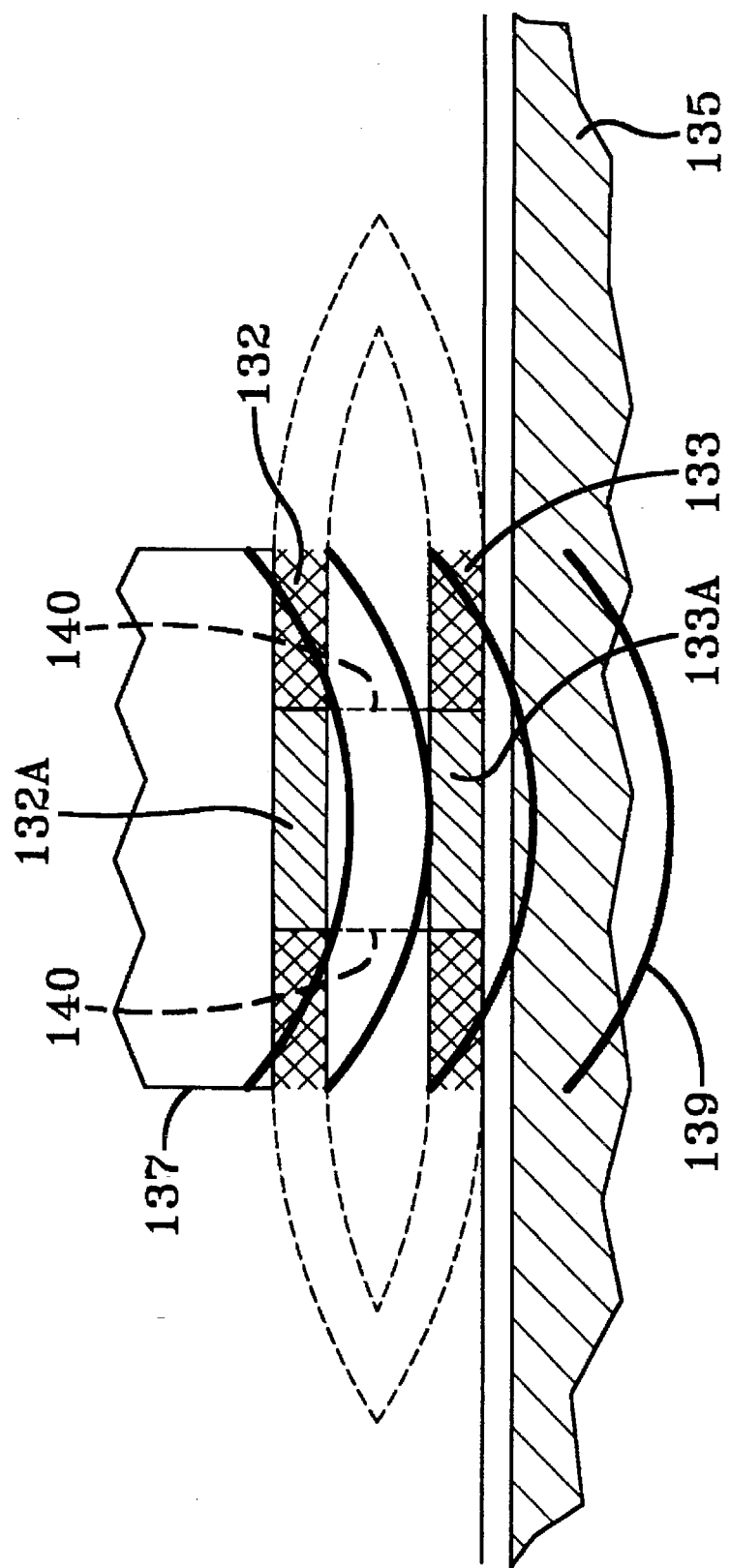
FIG. 11 is a cross-sectional view of a second embodiment of a pad constructed in accordance with the present invention in use in the first application thereof.
Figure 12:
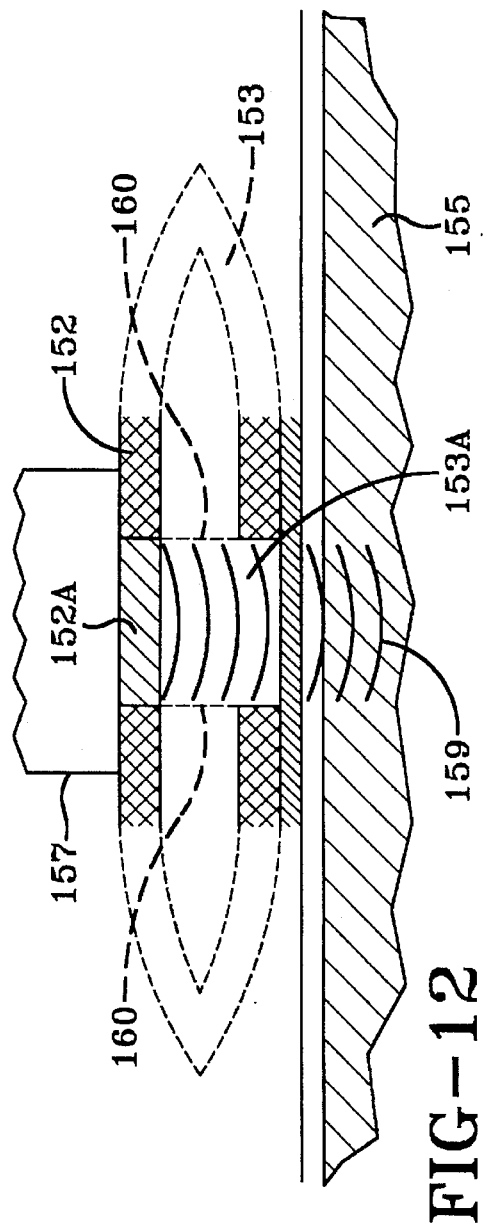
FIG. 12 is a cross-sectional view of a pad constructed in accordance with a third embodiment of the present invention.

In the embodiment of the present invention depicted in FIG. 11, first layer 102 and second layer 103 each have varying porosities along their lengths. First layer 102 includes first portion 132 and second portion 132A. Second layer 103 includes first portion 133 and second portion 133A. In this embodiment of the present invention, second portions 132A, 133A preferably overlie one another either in whole or in part, as depicted in FIG. 12. In addition, second portions 132A, 133A preferably are constructed of a material having a porosity sufficient to permit molecules of couplant 100 to become entrained in or to pass therethrough.

In one configuration of the embodiment of the present invention depicted in FIG. 11, first portions 132, 133 are constructed of a material having a pores which are substantially equal to the molecule size of couplant 100 such that molecules of couplant 100 become entrained in first portions 132, 133. In this configuration, second portions 132A, 133A are constructed of a material having pores which are larger than the molecule size of couplant 100 such that molecules of couplant 100 can pass therethrough. In this configuration, the amount of flow of couplant 100 from space 104 to ultrasound probe 137 and to target surface 135 can be controlled by adjusting the size and shape of second portions 132A, 133A, respectively. The acoustical wave pathway through pad 101 in this configuration is not limited because first and second layers 102, 103 provided an acoustical pathway from ultrasound probe 137 to target surface 135.

In a second configuration of the embodiment of the present invention depicted in FIG. 11, first portions 132, 133 are constructed of a material that is non-porous to molecules of couplant 100, i.e., a material constructed such that molecules of couplant 100 can neither become entrained therein or pass therethrough. In this configuration of the embodiment depicted in FIG. 11, second portions 132A, 133A are constructed of a material having pores which are at least as large as the molecule size of couplant 100 such that molecules of couplant 100 can become entrained therein or pass therethrough. In this configuration of the embodiment of the present invention depicted in FIG. 11, acoustical wave pathway 140 is defined through the pad and acoustical waves 139 pass only through acoustical wave pathway 140. That is, only the portion of acoustical waves 139 that passes through second portions 132A, 133A will be passed from ultrasound probe 137 to target surface 135. Changes to the size and/or shape of second portions 132A, 133A will alter the portion of acoustical wave 139 that reaches target surface 135 by altering acoustical wave pathway 140. It also will be appreciated that the amount of couplant 100 that becomes entrained in or passes through first and second layers 102, 103 can be controlled by adjusting the size of second portions 132A, 133A, i.e., the larger the areas of second portions 132A, 133A, the greater the flow rate of couplant through second layer 103.

In the embodiment of the present invention depicted in FIG. 12, second layer 103 has a varying porosity along its length due to the presence of one or more apertures defined through second layer 103. First layer 102 can have the same or different porosities along its length. For example, in one configuration of the embodiment of the present invention depicted in FIG. 12 first portion 152 of first layer 102 is constructed of a material that is not porous to couplant 100 while second portion 152A is constructed of a material having pores of a size sufficient to permit couplant 100 to become entrained therein or to pass therethrough. First portion 153 of second layer 103 is constructed of a material that is not porous to couplant 100. Apertures 153A can have a variety of different configurations and sizes. For example, if a high rate of flow of couplant 100 from pad 101 is desired, or if a high rate of transmission of acoustical waves 159 into target surface 155 is desired, apertures 153A can be larger than molecules of couplant 100, e.g., at least twice the size of molecules of couplant 100, or a plurality of apertures 153A can be provided. In contrast, if a relatively low flow rate of couplant 100 from pad 101 is desired, or if a relatively low rate of transmission of acoustical waves 159 into target 155 is desired, fewer apertures 153A and/or smaller apertures 153A, e.g., apertures greater than the size of molecules of couplant 100 but less than twice the size of molecules of couplant 100, will be employed. The pattern of acoustical waves 159 transmitted to target surface 155 can be controlled by selectively arranging apertures 153A in second layer 103. When first portion 152 of first layer 102 is constructed of a material that is not porous to couplant 100, second portion 152A of first layer 102 and apertures 152A preferably overlie one another either in whole or in part, as depicted in FIG. 12. In this configuration of the embodiment of the present invention depicted in FIG. 12, second portion 152A of first layer 102 overlies aperture 153A. Acoustical wave pathway 160 thus is defined through the pad depicted in FIG. 12 in this configuration. Couplant 100 can flow from space 104 through aperture 153A and onto target surface 155. The flow rate of couplant 100 can be selectively controlled by altering the size and number of apertures 153A.

In a second configuration of the embodiment of the present invention depicted in FIG. 12, first portion 152 of first layer 102 and first portion 153 of second layer 103 are constructed of a material having pores which are substantially equal to the molecule size of couplant 100 such that molecules of couplant 100 become entrained in first portions 152, 153. Second portion 152A of first layer 102 is constructed of a material having pores that are greater in size than the molecule size of couplant 100. One or more apertures 153A are formed through second layer 103. In this configuration, acoustical waves 159 emitted from an ultrasound probe 157 placed in contact with first layer 102 will be passed without interference through pad 101. Also in this configuration, couplant 100 can flow from space 104 through apertures 153A and onto target surface 155.

As above-referenced, the flow characteristics of the embodiment of the present invention depicted in FIG. 12 can be controlled by adjusting the size and number of apertures 153A. It also will be appreciated that the characteristics of an acoustical wave passing through pad depicted in FIG. 12 can be controlled by adjusting the size and shape of second portion 152A of first layer 102 and by adjusting the size and number of apertures 153A.

Figure 14:
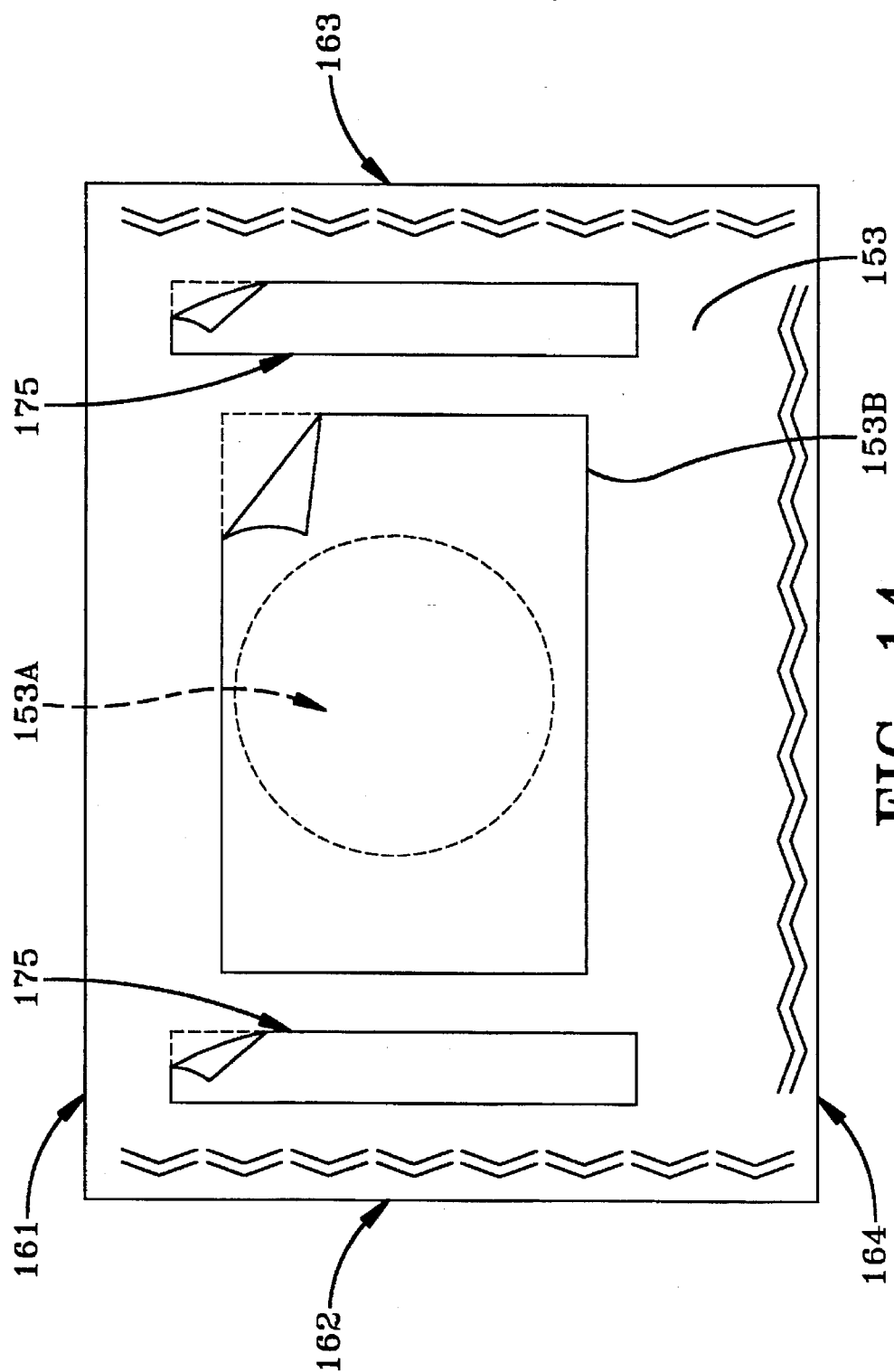
FIG. 14 is a bottom plan view of the pad of the third embodiment of the present invention.

In those embodiments of the present invention in which all or any portion of first and second layers 102, 103 are constructed of a material having a pore size greater than the molecule size of couplant 100, it is preferable that cover piece 153B be provided, as depicted in FIG. 12. Cover piece 153B is preferably constructed of a material that is not porous to couplant 100, i.e., a material having no pores or having pores of a size less than the size of the molecules of couplant 100. Cover piece 153B is disposed over the porous portion of first and second layers 102, 103, including aperture 153A as depicted in FIG. 14, and preferably is adhesively bound thereto such that cover piece 153B can be removed when delivery of couplant 100 is desired. It will be appreciated that cover piece 153B can be attached to first and second layers 102, 103 in other ways, including ultrasound welding. Cover piece 153B thus provides a fluid-tight seal over any portion of pad 101 that is constructed of a material having a pore size large enough such that molecules of couplant 100 can pass therethrough. In those embodiments where the porous portions of first and second layers 12, 103 are not porous until treated with a wetting agent, cover piece 153B can be omitted. However, it may be preferable to include cover piece 153B in these embodiments of the present invention in order to protect the porous portions of first and second layers 102, 103 and thereby to protect couplant 100.

In the embodiment of the present invention depicted in FIG. 14, adhesive strips 175 are provided on second layer 103. Adhesive strips 175 can be used to removably attach pad 101 to target surface 105, thereby preventing movement of pad 101 relative to target surface 105 during the ultrasound procedure. It will be appreciated that various known methods for retaining pad 101 relative to target surface 105 can be used in connection with the present invention, including, but not limited to, clamps and adhesive tape.

Figure 15:
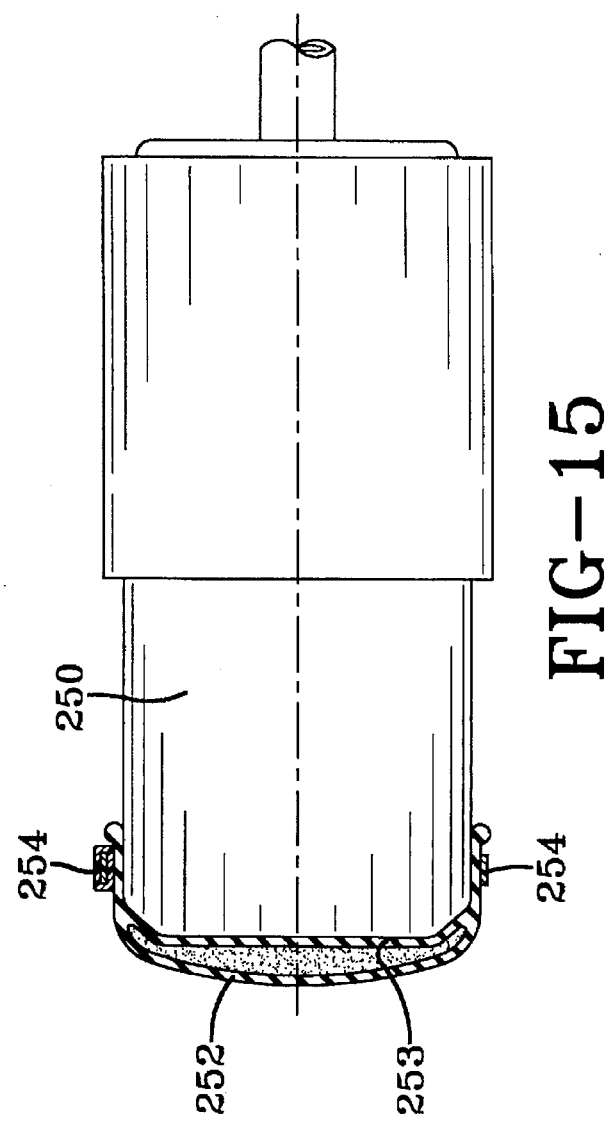
FIG. 15 is a side view, partially in section, of an ultrasound probe and pad constructed in accordance with the present invention.
Figure 16:
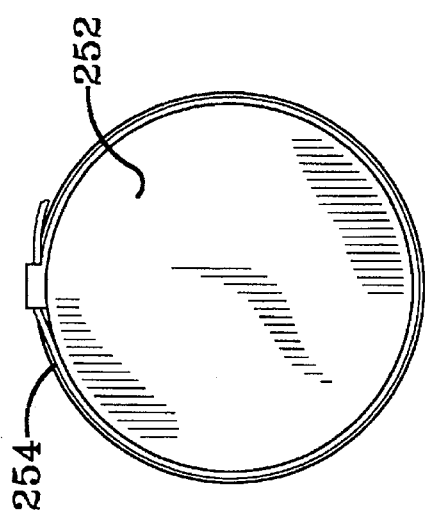
FIG. 16 is an end view of the ultrasound probe and pad depicted in FIG. 15.

As depicted in FIGS. 15 and 16, pad 101 can be detachably mounted on a ultrasound probe 250 using a variety of known attachment methods, thereby preventing movement of pad 101 relative to target ultrasound probe 250. For example, pad 101 can be adhesively mounted on ultrasound probe 250. As depicted in FIG. 15, pad 101 having first layer 252 and second layer 253 is mounted on ultrasound probe 250 using a mechanical attachment 254. In this embodiment, the periphery of first layer 252 and/or second layer 253 is extended in order to permit attachment with mechanical attachment 254. Mechanical attachment 254 can be a variety of known mechanisms, including hooks, clamps, and pins. As depicted, mechanical attachment 254 is a ring having a buckle mechanism which permits pad 101 to be detachably mounted on ultrasound probe 250.

Figure 17:
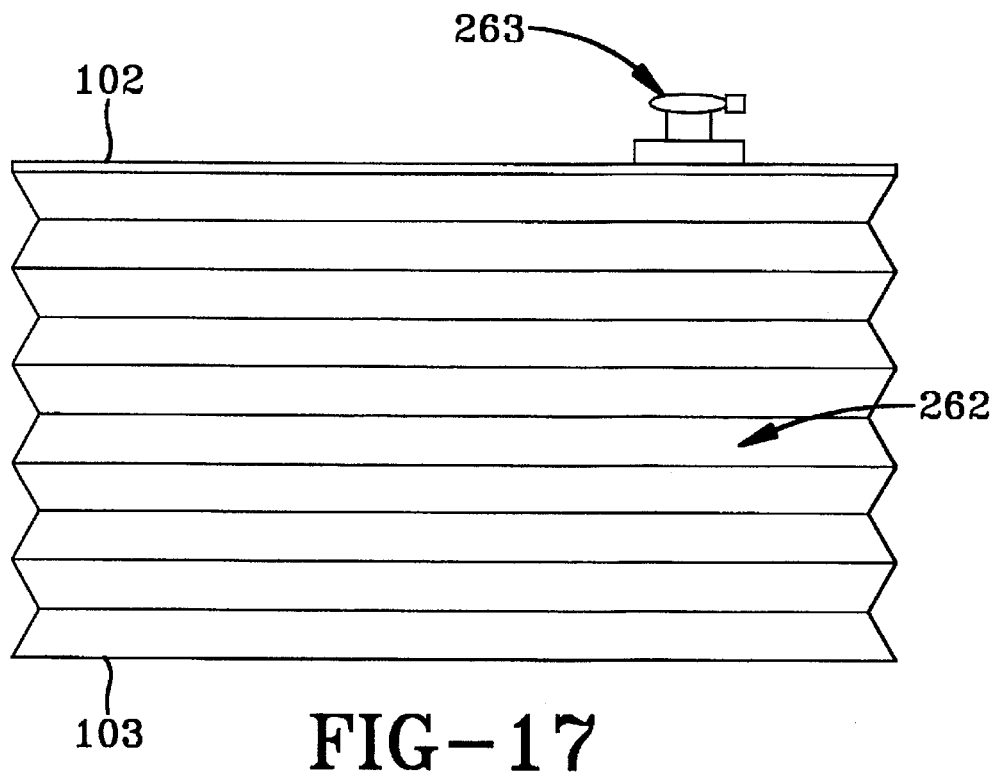
FIG. 17 is a perspective view of a fourth embodiment of a pad constructed in accordance with the present invention.
Figure 18:
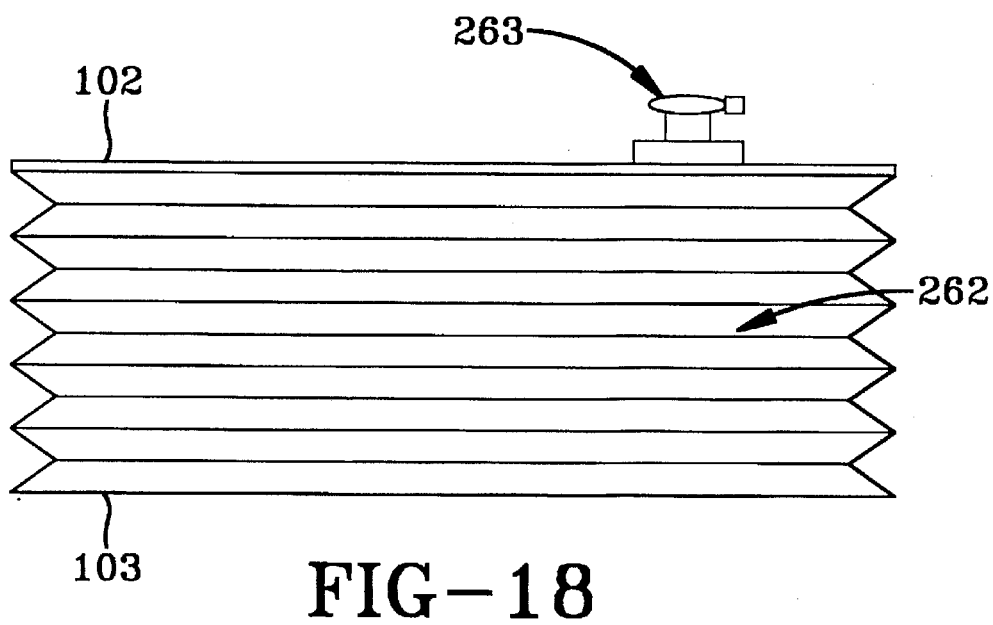
FIG. 18 is a perspective view of the fourth embodiment of a pad constructed in accordance with the present invention in a semi-collapsed state.
Figure 19:
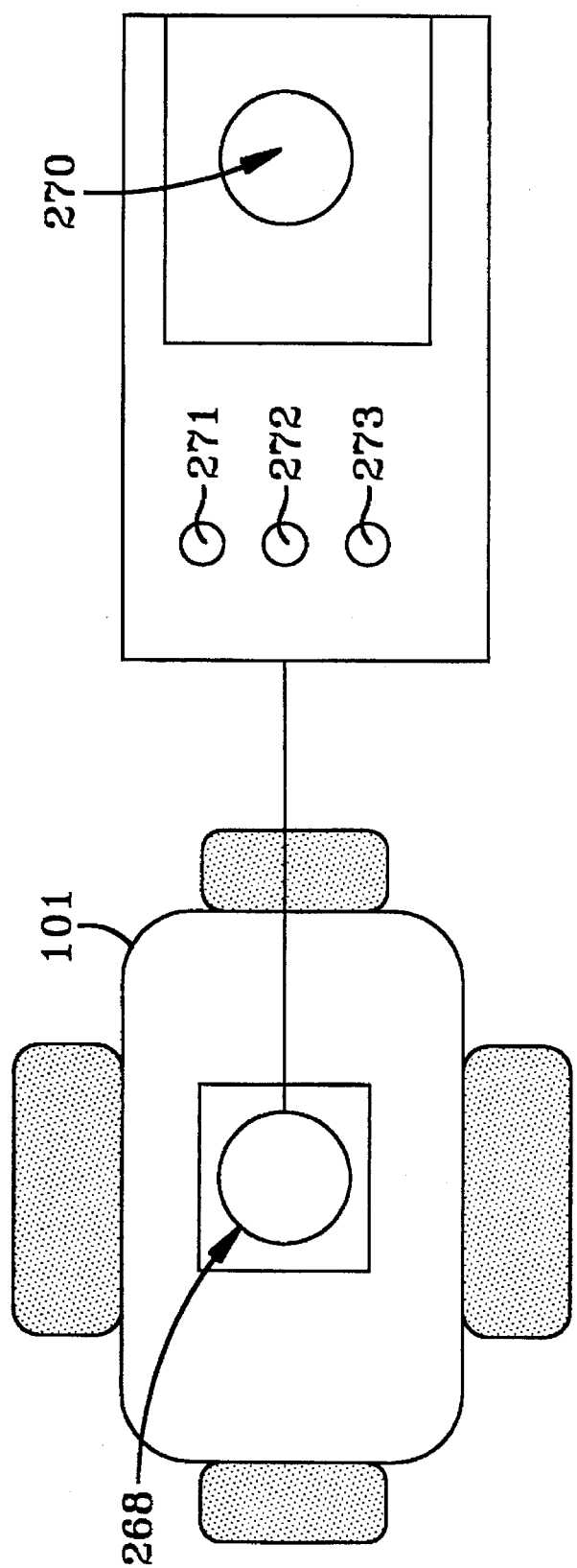
FIG. 19 is plan view of a system constructed in accordance with the present invention.

In the alternative embodiment of the present invention depicted in FIGS. 17–18, pad 101 is an expandable structure having first and second layers 102, 103. In this embodiment, pad 101 includes expandable side walls 262 which connect first layer 102 and second layer 103. Side walls 262, first layer 102, and second layer 103 define space 104 therein. Closable fill port 263 is provided on first layer 102 and is in fluid communication with space 104 such that couplant 100 can be selectively added to or removed from space 104. It will be appreciated that closable fill port 263 can be provided on any embodiment of the present invention. Side walls 262 are collapsible such that the volume of space 104 decreases as couplant 100 flows through first and/or second layer 102, 103. This configuration provides enhanced control of the pressure exerted on couplant 100 in space 104 and therefore affects the flow of couplant 100 into or through the porous portions of first and second layers 102, 103. That is, the flexible nature of pad 101 of this embodiment of the present invention substantially maintains the internal pressure of pad 101 and therefore substantially maintains the pressure exerted on couplant 100. In addition, the flexible nature of pad 101 of this embodiment of the present invention reduces or eliminates the occurrence of air bubbles within space 104 and prevents the creation of a void or an empty space within space 104 as couplant 100 flows through first and/or second layers 102, 103. The thickness of pad 101 depicted FIGS. 17 and 18 also can be selectively varied in order to adjust the ultrasound focusing point associated with different ultrasound applications. FIG. 17 depicts this embodiment in a fully extended condition while FIG. 18 depicts the embodiment of the present invention in a partially collapsed condition. It will be appreciated that structures other than the bellows-shaped side walls 262 depicted in FIGS. 17 and 18 can be used in order to render structure of pad 101 extendible in accordance with this embodiment of the present invention. For example, a telescoping structure could be used in lieu of the bellows.

In another embodiment of the present invention, an internal structure is provided within space 104 in order to exert a substantially constant pressure on couplant 100 in space 104. For example, a flexible wall can be provided in space 104 in order to define a pressure space that can be pressurized with gas or osmotically pressurized with a fluid. As couplant 100 flows from space 104 and into and/or through first and second layers 102, 103, the volume of couplant 100 in space 104 is reduced, thereby enabling the flexible membrane to expand so as to occupy the void left by couplant 100. Those of ordinary skill in the art will appreciate that various other configurations of this embodiment of the present invention are possible without departing from the intended scope and spirit of the present invention as defined in the claims. For example, the flexible wall can be connected to compression springs which urge it into a void in space 104 left by couplant 100 which has flowed from pad 101.

The embodiments of the present invention depicted in FIGS. 8, 9, and 11 can be used to conduct ultrasound waves to and/or from an ultrasound probe. For example, the embodiment of the present invention depicted in FIG. 8 can be used to facilitate ultrasound wave transmission to a target surface 105. In use, surface 106 of the depicted pad is placed in contact with target surface 105. Ultrasound probe 107 is then placed in contact with surface 108 of the depicted pad. Activation of ultrasound probe 107 will cause acoustic waves 109 to emanate therefrom. Because first and second layers 102, 103 are constructed of a material that permits couplant 100 to become entrained therein or to pass therethrough, ultrasound probe 107 will be in acoustic transmissive contact with target surface 105 such that acoustic waves 109 will pass through the pad and into target surface 105.

The embodiment of the present invention depicted in FIG. 9 is used by placing second layer 103 in contact with target surface 115 and placing ultrasound probe 117 in contact with first layer 102 of the pad. Because at least second portion 113A of second layer 103 and at least a portion of layer 102 are constructed of a material having pores of a sufficient constructed of a porous material that permits couplant 100 to become entrained therein or to pass therethrough, ultrasound probe 117 will be in acoustic transmissive contact with target surface 115. Activation of ultrasound probe 117 will cause acoustic waves 119 to emanate therefrom. As depicted in FIG. 9, ultrasound transmissive contact is created by both first portion 113 and second portion 113A of second layer 103 such that acoustic waves 119 pass through second layer 103 in their entirety, i.e., both first portion 113 and second portion 113A of second layer 103 are constructed of a material having a porosity that allows couplant 100 to become entrained therein or to pass therethrough. However, it will be appreciated that acoustic waves 119 will be "clipped" if first portion 113 of second layer 103 does not have a porosity that allows couplant 100 to become entrained therein or to pass therethrough and second portion 113A of second surface has a porosity that allows couplant 100 to become entrained therein or to pass therethrough. Thus, the configuration of second layer 103 and, more particularly, the relative sizes and positions of first portion 113 and second portion 113A of second layer 103 can be used to control, e.g., focus, acoustic waves 119. If second portion 113A is constructed of a material having a porosity that allows couplant 100 to pass therethrough, the volume of couplant 100 released from pad 101 through second layer 103 can be controlled by selectively altering the size of second portion 113A.

The embodiment of the present invention depicted in FIG. 11 is used by placing second layer 103 in contact with target surface 135 and by placing ultrasound probe 137 in contact with first layer 102 of the pad. Because at least second portions 132A, 133A of first and second layers 102, 103 are constructed of a porous material that permits couplant 100 to become entrained therein or to pass therethrough, ultrasound probe 137 will be in acoustic transmissive contact with target surface 135. Activation of ultrasound probe 117 will cause acoustic waves 139 to emanate therefrom. As depicted in FIG. 11, ultrasound transmissive contact is created by both first portion 133 and second portion 133A of second layer 103 such that acoustic waves 139 pass through second layer 133 in their entirety when first portion 133 second layer 103 is constructed of a material having a porosity that allows couplant 100 to become entrained therein or to pass therethrough. However, it will be appreciated that acoustic waves 139 will be "clipped" if first portion 133 of second layer 103 does not have a porosity that allows couplant 100 to become entrained therein or to pass therethrough, provided second portion 133A of second surface has a porosity that allows couplant 100 to become entrained therein or to pass therethrough. Thus, the configuration of second layer 103 and, more particularly, the relative sizes and positions of second portions 132A, 133A can be used to control, e.g., focus, acoustic waves 119. If second portion 133A is constructed of a material having a porosity that allows couplant 100 to pass therethrough, the volume of couplant 100 released from the pad can be controlled by selectively altering the size of second portion 133A.

Pad 101 of the present invention can be used in a wide variety of applications in which ultrasound probes are used, e.g., industrial analysis of structural features, industrial analysis of package contents, medical diagnosis/imaging, and medical treatment. Due to the configuration of pad 101, it can be used with various configurations of ultrasound probes in connection with the transmission and/or reception of ultrasound waves. As above-discussed, the term "ultrasound probe" identifies an apparatus that emits and/or receives ultrasound waves.

In another alternative embodiment of the method of the present invention, pad 101 can be used for the purpose of introducing a fluid through the skin of a patient and/or into a target body tissue. In this method of the present invention, pad 101 is provided, wherein pad 101 is constructed in accordance with any of the above-discussed embodiments of the present invention in which all or any portion of second layer 103 is constructed of a porous material having pores of a size sufficient to permit molecules of couplant 100 to pass therethrough and in which any portion of first layer 102 is constructed of a material having pores of a size sufficient to allow couplant 100 to become entrained therein or to pass therethrough. In this embodiment of the method of the present invention, couplant 100 preferably comprises a medical product such as a pharmaceutical or imaging agent which is to be delivered to a target body tissue. For example, the medical product can be dissolved in or suspended in couplant 100 and preferably has a molecule size less than the molecule size of couplant 100. Alternatively, couplant 100 can be the medical product itself.

It will be appreciated that the target surface in this method of the present invention can be any body tissue that is accessible from the exterior of the body using known medical techniques. For example, pad 101 can be configured to be placed on the skin of a patient in order to effect a transcutaneous delivery of couplant 100. In the alternative, pad 101 can be configured to be inserted into the body such that it can be placed in direct contact with an internal body tissue using laparascopic insertion techniques, surgical probes, catheters, etc.

In this embodiment of the method of the present invention, an ultrasound probe of known construction also is provided. Second layer 103 of pad 101 is placed in contact with the target body tissue and the ultrasound probe is placed in contact with first layer 102. The ultrasound probe is then activated so as to generate an acoustical wave pattern therefrom. Due to the fact that at least a portion of second layer 103 is constructed of a material having a pore size sufficient to permit molecules of couplant 100 to pass therethrough, couplant 100 will flow from space 104 onto the target surface. Ultrasound transmissive contact is thus established between the ultrasound probe and the target surface due to the fact that at least a portion of first layer 102 is constructed of a material having pores of sufficient size to permit couplant 100 to become entrained therein or to pass therethrough. The acoustical waves thus are delivered to the target surface where they will cause a disorientation of the body tissue which will facilitate the transport of couplant 100 into the body tissue. In this method of the present invention, the volume of couplant 100 delivered to the body tissue can be controlled by (a) selectively controlling the energy level of the acoustical waves generated by the ultrasound probe; (b) selectively controlling the frequency of the acoustical waves generated by the ultrasound probe; (c) selectively controlling the duration of the delivery of acoustical waves from the ultrasound probe; (d) selectively controlling the size of the pores or the aperture formed through second layer 103 of pad 101; and/or (e) selectively controlling the size or volume of pad 101. It will be appreciated that the volume of medical product delivered to the target body tissue can be controlled by selectively varying the concentration of the medical product in couplant 100 where the medical product is dissolved in or suspended in couplant 100. In the event that either first layer or second layer 102, 103 is constructed of a material that is not porous to couplant 100 without treatment, as above discussed, this method of the present invention will further include the step of delivering a wetting agent, e.g., isopropyl alcohol, to first layer and/or second layer 102, 103 for the purpose of rendering one or both of layers 102, 103 porous to couplant 100.

In another alternative embodiment of the method of the present investigation, pad 101 is provided wherein pad 101 is constructed in accordance with any of the above-referenced embodiments. An ultrasound probe of known construction and a medical product such as a pharmaceutical or an imaging agent also are provided. The medical product is placed in direct contact with a target body tissue. Second layer 103 of pad 101 is then placed in contact with the medical product and the ultrasound probe is placed in contact with first layer 102 of pad 101. The ultrasound probe is then activated so as to generate an acoustical wave pattern therefrom. Due to the fact that at least a portion of second layer 103 is constructed of a material having a pore size sufficient to permit molecules of couplant 100 to become entrained therein or to pass therethrough, and due to the fact that at least a portion of first layer 102 is constructed of a material having a pore size sufficient to permit molecules of couplant 100 to become entrained therein or to pass therethrough, ultrasound transmissive contact is established between the ultrasound probe and the target body tissue surface. The acoustical waves thus are delivered to the target surface where they will cause a disorientation of the body tissue which will facilitate the transport of medical product into the target body tissue. In this method of the present invention, the volume of medical product delivered to the body tissue can be controlled by (a) selectively controlling the energy level of the acoustical waves generated by the ultrasound probe; (b) selectively controlling the frequency of the acoustical waves generated by the ultrasound probe; (c) selectively controlling the duration of the delivery of acoustical waves from the ultrasound probe; and/or (d) selectively controlling the size of the pores or the aperture formed through second layer 103 of pad 101. The volume of medical product delivered to the target body tissue can further be controlled by selectively varying the concentration of the medical product applied to the target body tissue. In the event that either first layer or second layer 102, 103 is constructed of a material that is not porous to couplant 100 without treatment, as above discussed, this method of the present invention will further include the step of delivering a wetting agent to first layer and/or second layer 102, 103 for the purpose of rendering one or both of layers 102, 103 porous to couplant 100.

In another alternative embodiment of the present invention depicted in FIG. 21, pad 101 is provided where pad 101 is constructed in accordance with any of the above-referenced embodiments of the present invention. In this embodiment, couplant 100 comprises a medical product such as a pharmaceutical or an imaging agent. First layer 102 of pad 101 is mounted in contact with ultrasound probe 268 of known construction. In this embodiment, ultrasound probe 268 preferably is connected via connector 275 to a central control unit 269 which is constructed to activate and deactivate ultrasound probe 268. In the preferred configuration of this embodiment, central control unit 269 is adapted such that the energy level, frequency, duration of activation, and interval between activation of ultrasound probe 268 by central control unit 269 can be selectively controlled by an operator. For example, central control unit 269 can include controls as generally indicated at 270, 271, 272, and 273 in FIG. 21 which enable an operator to select the desired operation of ultrasound probe 268. This embodiment of the present invention can be adapted to be worn by a patient such that the patient can be mobile as medical product is delivered to target tissue in the manner above-discussed.

The embodiment of the present invention depicted in FIG. 21 can further include a means for sampling a body tissue or a body fluid and a means for analyzing the tissue or fluid sample. The means for sampling can entail a variety of techniques including ultrasound sampling. The means for analyzing can be any of a variety of known devices useful in analyzing tissue and/or fluid samples. In this embodiment, central control unit 269 is adapted to interpret the results of the analysis and to activate probe 268 in order to correct any abnormalities between the results of the tissue or fluid analysis and a predetermined desired state.

This embodiment of the present invention can be configured to sample body fluids and to conduct an analysis thereof. The results of the analysis by the means for analyzing are interpreted by central control unit 269 and compared to a standard, acceptable range for a body fluid parameter. If central control unit 269 determines that the level is not within an acceptable range, it will activate ultrasound probe 268 such that couplant 100 are allowed to enter a target tissue of the patient, e.g., the skin. The energy level, frequency, and duration of operation of ultrasound probe 268 will be dependent upon the degree to which the body fluid must be adjusted.

Although the apparatus and method of the present invention have been described herein with respect to certain preferred embodiments, it will become apparent to one of ordinary skill in the art that various modifications can be made to these embodiments. Such modifications are intended to be within the spirit and scope of the present invention as defined in the appended claims.

What is claimed is:

1. A method for conducting an ultrasound procedure on an object having a target surface, said method comprising the steps of:

providing an ultrasound probe having an acoustical wave emitting end portion;

providing a pad for transmitting acoustical waves between said ultrasound probe and a target surface of an object, said pad comprising:

a first layer having a first porous portion, said first porous portion defining first layer pores therethrough, said first layer pores having a first layer pore dimension;

a second layer having a first porous portion, said first porous portion defining second layer pores therethrough, said second layer attached to said first layer, said first and second layers defining a space therebetween, said second layer pores having a second layer pore dimension, said first porous portion of said first layer overlying said first porous portion of said second layer; and an ultrasound couplant disposed in said space defined between said first layer and said second layer, said ultrasound couplant having a molecule size, said molecule size being less than or substantially equal to said first layer pore dimension, and said molecule size being less than or substantially equal to said second layer pore dimension, whereby said ultrasound couplant becomes entrained in or passes through said first porous portions of said first and second layers, and whereby acoustical waves can be transmitted from said first layer to said second layer;

placing said first porous portion of said second layer in contact with a target surface;

placing said acoustical wave emitting end portion of said ultrasound probe in contact with said first porous portion of said first layer; and activating said ultrasound probe whereby acoustical waves are emitted from said acoustical wave emitting end portion of said ultrasound probe, thereby directing acoustical waves to said target surface.

2. A method for conducting an ultrasound procedure on an object having a target surface in accordance with claim 1, wherein said second layer pore dimension is greater than said molecule size of said ultrasound couplant and wherein said ultrasound couplant comprises a medical product.

3. A method for conducting an ultrasound procedure on an object having a target surface in accordance with claim 2, wherein said medical product is selected from a group consisting of pharmaceuticals and imaging agents.

4. A method for conducting an ultrasound procedure on an object having a target surface in accordance with claim 1, wherein said method further comprises the steps of providing a means for selectively activating said ultrasound probe, and coupling said means for selectively activating said ultrasound probe to said ultrasound probe.

5. A method for conducting an ultrasound procedure on an object having a target surface in accordance with claim 4, wherein said means for selectively activating said ultrasound probe has a programmable energy level, and wherein said method further comprises the step of programming said means for selectively activating said ultrasound probe to a selected energy level.

6. A method for conducting an ultrasound procedure on an object having a target surface in accordance with claim 4, wherein said means for selectively activating said ultrasound probe has a programmable frequency, and wherein said method further comprises the step of programming said means for selectively activating said ultrasound probe to a selected frequency.

7. A method for conducting an ultrasound procedure on an object having a target surface in accordance with claim 4, wherein said means for selectively activating said ultrasound probe has a programmable duration for activation of said ultrasound probe, and wherein said method further comprises the step of programming said means for selectively activating said ultrasound probe to a selected duration for activation of said ultrasound probe.

8. A method for conducting an ultrasound procedure on an object having a target surface in accordance with claim 4, wherein said means for selectively activating said ultrasound probe has a programmable delay period, and wherein said method further comprises the step of programming said means for selectively activating said ultrasound probe to a selected delay period.

9. A method for delivering a medical product to a target body tissue, said method comprising the steps of:

providing an ultrasound probe having an acoustical wave emitting end portion;

providing a pad for transmitting acoustical waves between said ultrasound probe and a surface of a target body tissue, said pad comprising:

a first layer having a first porous portion, said first porous portion defining first layer pores therethrough, said first layer pores having a first layer pore dimension;

a second layer having a first porous portion, said first porous portion defining second layer pores therethrough, said second layer attached to said first layer, said first and second layers defining a space therebetween, said second layer pores having a second layer pore dimension, said first porous portion of said first layer overlying said first porous portion of said second layer; and an ultrasound couplant disposed in said space defined between said first layer and said second layer, said ultrasound couplant comprising a medical product, said ultrasound couplant having a molecule size, said molecule size being less than or substantially equal to said first layer pore dimension, and said molecule size being less than said second layer pore dimension, whereby said ultrasound couplant becomes entrained in or passes through said first porous portion of said first layer, whereby said ultrasound couplant passes through said first porous portion of said second layer, and whereby acoustical waves can be transmitted from said first layer to said second layer;

placing said first porous portion of said second layer in contact with a surface of a target body tissue;

placing said acoustical wave emitting end portion of said ultrasound probe in contact with said first porous portion of said first layer; and activating said ultrasound probe whereby acoustical waves are emitted from said acoustical wave emitting end portion of said ultrasound probe, and whereby said acoustical waves disrupt said surface of a target body tissue, thereby facilitating delivery of said couplant to the target body tissue.

10. A method for delivering a medical product to a target body tissue in accordance with claim 9, wherein said medical product is selected from a group consisting of pharmaceuticals and imaging agents.

11. A method for delivering a medical product to a target body tissue, said method comprising the steps of:

providing an ultrasound probe having an acoustical wave emitting end portion;

providing a pad for transmitting acoustical waves between said ultrasound probe and a surface of a target body tissue, said pad comprising:

a first layer having a first porous portion, said first porous portion defining first layer pores therethrough, said first layer pores having a first layer pore dimension;

a second layer having a first porous portion, said first porous portion defining second layer pores therethrough, said second layer attached to said first layer, said first and second layers defining a space therebetween, said second layer pores having a second layer pore dimension, said first porous portion of said first layer overlying said first porous portion of said second layer; and an ultrasound couplant disposed in said space defined between said first layer and said second layer, said ultrasound couplant having a molecule size, said molecule size being less than or substantially equal to said first layer pore dimension, and said molecule size being less than or substantially equal to said second layer pore dimension, whereby said ultrasound couplant becomes entrained in or passes through said first porous portions of said first and second layers, and whereby acoustical waves can be transmitted from said first layer to said second layer;

placing a medical product in contact with a surface of a target body tissue;

placing said first porous portion of said second layer in contact with said medical product;

placing said acoustical wave emitting end portion of said ultrasound probe in contact with said first porous portion of said first layer; and activating said ultrasound probe, whereby acoustical waves are emitted from said acoustical wave emitting end portion of said ultrasound probe, and whereby said acoustical waves disrupt said surface of a target body tissue, thereby facilitating delivery of said medical product to the target body tissue.

12. A method for delivering a medical product to a target body tissue in accordance with claim 11, wherein said medical product is selected from a group consisting of pharmaceuticals and imaging agents.

13. A method for conducting an ultrasound procedure on an object having a target surface, said method comprising the steps of:

providing an ultrasound probe having an acoustical wave emitting end portion;

providing a pad for transmitting acoustical waves between said ultrasound probe and a target surface of an object, said pad comprising:

a first layer having a first porous portion, said first porous portion defining first layer pores therethrough, said first layer pores having a first layer pore dimension;

a second layer having at least one aperture formed therethrough, said at least one aperture having an aperture dimension, said second layer attached to said first layer, said first and second layers defining a space therebetween, said first porous portion of said first layer overlying said at least one aperture formed through said second layer; and an ultrasound couplant disposed in said space defined between said first layer and said second layer, said ultrasound couplant having a molecule size, said molecule size being less than or substantially equal to said first layer pore dimension, and said molecule size being less than or substantially equal to said aperture dimension, whereby said ultrasound couplant becomes entrained in or passes through said first porous portion of said first layer, whereby said ultrasound couplant becomes entrained in or passes through said at least one aperture formed through said second layer, and whereby acoustical waves can be transmitted from said first layer to said second layer;

placing said at least one aperture formed through said second layer in contact with a target surface;

placing said acoustical wave emitting end portion of said ultrasound probe in contact with said first porous portion of said first layer; and activating said ultrasound probe whereby acoustical waves are emitted from said acoustical wave emitting end portion of said ultrasound probe.

14. A method for conducting an ultrasound procedure on an object having a target surface in accordance with claim 13, wherein said ultrasound couplant comprises a medical product.

15. A method for conducting an ultrasound procedure on an object having a target surface in accordance with claim 14, wherein said medical product is selected from a group consisting of pharmaceuticals and imaging agents.

* * * * *